United States Patent
Duan et al.

(10) Patent No.: US 12,161,311 B2
(45) Date of Patent: Dec. 10, 2024

(54) AUXILIARY APPARATUS FOR MINIMALLY INVASIVE SURGERY AND METHOD TO USE THE SAME

(71) Applicants: Ankon Medical Technologies (Shanghai) Co., LTD, Shanghai (CN); ANX IP HOLDING PTE. LTD., Singapore (SG)

(72) Inventors: Xiaodong Duan, Pleasanton, CA (US); Yakun Ma, Shanghai (CN)

(73) Assignees: ANKON MEDICAL TECHNOLOGIES (SHANGHAI) CO., LTD., Shanghai (CN); ANX IP HOLDING PTE. LTD., Singapore (SG)

( * ) Notice: Subject to any disclaimer, the term of this patent is extended or adjusted under 35 U.S.C. 154(b) by 835 days.

(21) Appl. No.: 17/298,001

(22) PCT Filed: Dec. 30, 2018

(86) PCT No.: PCT/CN2018/125924
§ 371 (c)(1),
(2) Date: May 27, 2021

(87) PCT Pub. No.: WO2020/107636
PCT Pub. Date: Jun. 4, 2020

(65) Prior Publication Data
US 2021/0393253 A1    Dec. 23, 2021

(30) Foreign Application Priority Data
Nov. 27, 2018 (CN) .......................... 201811423746.8

(51) Int. Cl.
A61B 17/02    (2006.01)
A61B 17/00    (2006.01)
(Continued)

(52) U.S. Cl.
CPC .......... *A61B 17/0218* (2013.01); *A61B 34/30* (2016.02); *A61B 34/73* (2016.02); *A61B 2017/00039* (2013.01)

(58) Field of Classification Search
CPC ..... A61B 17/0218; A61B 34/30; A61B 34/73; A61B 2017/00039; A61B 2034/2051;
(Continued)

(56) References Cited

U.S. PATENT DOCUMENTS 6,216,028 B1 * 4/2001 Haynor .................... A61B 5/06
128/899
2007/0135678 A1 * 6/2007 Suzuki ............... A61B 17/0487
600/37

(Continued)

FOREIGN PATENT DOCUMENTS

CN    103637803 A    3/2014
CN    103932654 A    7/2014
(Continued)

*Primary Examiner* — Sunita Reddy
(74) *Attorney, Agent, or Firm* — Treasure IP Group, LLC

(57) ABSTRACT

An auxiliary apparatus for minimally invasive surgery is provided. The auxiliary apparatus includes an in vivo device, an in vitro device, a locating probe and a control system. The in vitro device includes an in vitro magnetic field generating element and a driving mechanism. The in vivo device includes a magnetic auxiliary member and a clip. The locating probe includes a magnetic field sensor. The auxiliary apparatus can achieve the effects of easy control of the mucosa curling angle, high repeatability of operation, fast speed, high safety and reliability for the mucosa to be dissected in any spatial orientation.

12 Claims, 5 Drawing Sheets

(51) Int. Cl.
*A61B 34/00* (2016.01)
*A61B 34/30* (2016.01)

(58) Field of Classification Search
CPC ............ A61B 2034/731; A61B 17/083; A61B 2017/00269; A61B 2017/00017; A61B 17/00234; A61B 2017/00345
USPC .................................................. 128/897–899
See application file for complete search history.

(56) References Cited

U.S. PATENT DOCUMENTS

| | | | |
|---|---|---|---|
| 2009/0043246 A1* | 2/2009 | Dominguez | A61B 34/70 604/21 |
| 2011/0240044 A1* | 10/2011 | Duan | A61B 1/041 128/899 |
| 2012/0221016 A1* | 8/2012 | Fell | A61B 34/30 901/23 |
| 2012/0310034 A1* | 12/2012 | Creighton | A61P 9/08 977/773 |
| 2013/0289581 A1* | 10/2013 | Yeung | A61B 34/73 606/130 |
| 2014/0094681 A1 | 4/2014 | Valentine et al. | |
| 2015/0057676 A1* | 2/2015 | Muntwyler | A61B 17/00234 606/130 |
| 2015/0380140 A1* | 12/2015 | Duan | H01F 7/0257 600/109 |
| 2017/0035407 A1* | 2/2017 | Duan | A61B 34/73 |
| 2017/0035520 A1* | 2/2017 | Duan | A61B 1/041 |
| 2019/0321472 A1* | 10/2019 | Creighton | A61N 2/06 |
| 2021/0128125 A1* | 5/2021 | Sitti | A61B 1/041 |

FOREIGN PATENT DOCUMENTS

| | | |
|---|---|---|
| CN | 104323778 | 2/2015 |
| CN | 104546119 A | 4/2015 |
| CN | 201310136094.0 | 9/2015 |
| CN | 201510661964.5 | 3/2019 |
| DE | 102013202324 A | 8/2014 |
| JP | 2007190164 A | 8/2007 |
| JP | 2018515312 A | 6/2018 |
| WO | 2008131128 A1 | 10/2008 |
| WO | 2010041714 | 4/2010 |

* cited by examiner

AUXILIARY APPARATUS FOR MINIMALLY INVASIVE SURGERY AND METHOD TO USE THE SAME

CROSS-REFERENCE TO RELATED APPLICATIONS

The application claims priority to Chinese patent application No. 201811423746.8 filed on Nov. 27, 2018, which is titled "auxiliary apparatus for minimally invasive surgery and method to use the same", the contents of which are incorporated by reference herein.

FIELD OF INVENTION

The present disclosure relates to an auxiliary apparatus for minimally invasive surgery, and, more particularly, to an auxiliary apparatus for minimally invasive surgery and a control method to enlarge the visual field of surgery.

BACKGROUND

Minimally invasive surgery (MIS), as a treatment modality that changes the classical operative surgical technique, has won the favor of hospitals and doctors for its advantages such as less bleeding, smaller incisions, less impact on organ functions, faster recovery, and fewer postoperative complications, and has made substantial breakthroughs and applications in many surgical procedures. While the advantages of minimally invasive surgery are increasingly recognized, its shortcomings are gradually becoming apparent, such as longer learning time and higher operational precision requirements for physicians. Traditional surgical instruments no longer meet the needs and require continuous improvement or even complete innovation, and the technical aspects involved are not only extensive, but also require cutting-edge technological innovations to be incorporated to meet the special needs required for minimally invasive surgery.

Endoscopic submucosal dissection (ESD) is an endoscopic treatment technique applied in early carcinoma or precancerous surgery targets of the gastrointestinal tract, and ESD treatment allows complete dissection of diseased mucosa. In order to facilitate the operations of a surgeon and reduce postoperative complications, using an external magnetic field for stretching during the procedure is beginning to gain attention. A cylindrical magnet is fixed to an end of a hemostatic clip with a flexible connective thread, and the hemostatic clip is anchored on the edge of the mucosa after a pre-cut around the mucosa using ESD is completed. Finally, the external magnetic field is used to guide the cylindrical magnet, driving the hemostatic clip to stretch on the mucosal layer and make it curl, so that the ESD procedure is performed under a clear field of view with less difficulty.

Since the mucosa to be dissected can be in any spatial location within the digestive tract, its normal has any orientation in space. However, the specific spatial location of the mucosa cannot be obtained only through images captured by an endoscope, which makes it difficult for the external magnetic field to precisely control the curling of mucosa in a desired direction. A method of only relying on the operator to observe the direction of motion of the cylindrical magnet relative to the mucosa in a process of trial and error to control the direction of the external magnetic field for mucosa curling is difficult, with low repeatability, long duration and low safety, and is not conducive to the promotion and application of magnetic stretching technology in clinical practice of ESD.

Therefore, it is necessary to provide an auxiliary apparatus for MIS and a method to use the same.

SUMMARY OF THE INVENTION

The present invention aims at the disadvantages of the previous art to provide an auxiliary apparatus for minimally invasive surgery and a method to use the same.

The present invention provides an auxiliary apparatus for minimally invasive surgery, comprising an in vivo device, an in vitro device, a locating probe and a control system. The in vitro device comprises an in vitro magnetic field generating element that provides a magnetic field for rotating and a driving mechanism that drives the in vitro magnetic field generating element to move and/or rotate. The in vivo device comprises a magnetic auxiliary member and a clip connected to the magnetic auxiliary member. The locating probe comprises a magnetic field sensor for detecting the magnetic field intensity of the in vitro magnetic field generating element. Both the driving mechanism and the locating probe are directly or indirectly communicating with the control system.

In one embodiment, the driving mechanism comprises a motor controlled by the control system, a robotic arm or a two-degree-of-freedom turntable driven by the motor to move and/or rotate the in vitro magnetic field generating element.

In another embodiment, the magnetic auxiliary member comprises a first limit member, a second limit member and at least one magnetic cylinder disposed between the first limit member and the second limit member, and a connective thread. The first limit member comprises a first through hole. The second limit member comprises a second through hole. The magnetic cylinder comprises a third through hole. The connective thread passes through the first through hole, the third through hole and the second through hole to join the first limit member, at least one magnetic cylinder and the second limit member together.

In another embodiment, the magnetic field sensor is a magnetic field sensor based on magnetoresistive effect, or a Hall sensor.

In another embodiment, the in vitro device and the locating probe are configured such that: when the locating probe is placed at the center of the pre-cut mucosa to be dissected, the driving mechanism drives the in vitro magnetic field generating element to move; and when the magnetic field intensity detected by the locating probe reaches a peak value, the in vitro magnetic field generating element stops at its current position and does not move again.

In another embodiment, the in vitro device and the in vivo device are configured such that:

when the in vivo device is placed on the edge of the mucosa to be dissected, the clip clips the mucosa to be dissected and the in vitro magnetic field generating element generates an in vitro magnetic field, the control system defines 2 rotational degrees of freedom of an in vitro magnetic dipole according to a default trajectory generator and the driving mechanism drives the in vitro magnetic field generating element so that the in vitro magnetic dipole rotates a combination of the 2 rotational degrees of freedom, and the magnetic auxiliary member moves and/or rotates accordingly with the rotation of the in vitro magnetic field generating element.

In another embodiment, the in vitro device and the in vivo device are configured such that:

the driving mechanism drives the in vitro magnetic field generating element to rotate, the magnetic auxiliary member moves and/or rotates accordingly with the rotation of the in vitro magnetic field generating element, while the magnetic auxiliary member is adjusted to a position P1' flat against the mucosa to be dissected, and the control system records the position of the in vitro magnetic dipole as a first flat position P1;

the driving mechanism drives the in vitro magnetic field generating element to rotate, the magnetic auxiliary member moves and/or rotates accordingly with the rotation of the in vitro magnetic field generating element, while the magnetic auxiliary member is adjusted to another position P2' flat against the mucosa to be dissected, and the control system records the position of the in vitro magnetic dipole as a second flat position P2, the first flat position P1 and the second flat position P2 forming a plane S, the position P1' and the position P2' forming a plane S';

the control system defines the 2 rotational degrees of freedom for the rotation of the in vitro magnetic dipole as follows: the 1st' rotational degree of freedom is rotation in the plane S and the 2nd' rotational degree of freedom is rotation about the rotation axis obtained by a cross product of the normal vector of the plane S and the second flat position P2;

the driving mechanism drives the in vitro magnetic dipole to rotate the 1st' rotational degree of freedom, then the magnetic auxiliary member rotates in the plane S' of mucosa, and the magnetic auxiliary member is adjusted to the center of the plane S' of mucosa or other initial position of curling;

the driving mechanism drives the in vitro magnetic dipole to rotate the 2nd' rotational degree of freedom, then the magnetic auxiliary member starts to curl.

In another embodiment, the default trajectory generator is configured to:

build in the control system a carrier coordinate system O-XYZ of the in vitro magnetic dipole, and define the two rotational degrees of freedom of the in vitro magnetic dipole in the carrier coordinate system as rotation about the X-axis and Z-axis, respectively; where the direction of the in vitro magnetic dipole is taken as the Y-axis direction, and the X-axis and Z-axis are the coordinate axes selected in the plane perpendicular to the Y-axis, and the X-axis, Y-axis and Z-axis conform to the right-hand rule.

In another embodiment, the control system is configured such that:

after the in vitro magnetic dipole rotates a combination of the 2 rotational degrees of freedom, and the control system records the first flat position P1 and the second flat position P2 of the in vitro magnetic dipole, the control system updates the trajectory generator according to the first flat position P1 and the second flat position P2, and the control system enters a state of mucosa curling.

In another embodiment, the in vitro device and the in vivo device are configured such that:

when the in vivo device is placed on the edge of the mucosa to be dissected, the clip clips the mucosa to be dissected and the in vitro magnetic field generating element generates an in vitro magnetic field, the control system builds a carrier coordinate system O-XYZ of the in vitro magnetic dipole, and defines the 2 rotational degrees of freedom of the in vitro magnetic dipole in the carrier coordinate system as rotation about the X-axis and Z-axis, respectively; where the direction of the in vitro magnetic dipole is taken as the Y-axis direction, and the X-axis and Z-axis are the coordinate axes selected in the plane perpendicular to the Y-axis, and the X-axis, Y-axis and Z-axis conform to the right-hand rule;

the driving mechanism drives the in vitro magnetic field generating element to make the in vitro magnetic dipole rotate a combination of the 2 rotational degrees of freedom, the magnetic auxiliary member moves and/or rotates accordingly with the rotation of the in vitro magnetic field generating element, while the magnetic auxiliary member is adjusted to a position P1' flat against the mucosa to be dissected, and the control system records the position of the in vitro magnetic dipole as a first flat position P1;

the driving mechanism drives the in vitro magnetic field generating element to make the in vitro magnetic dipole rotate a combination of the 2 rotational degrees of freedom, the magnetic auxiliary member moves and/or rotates accordingly with the rotation of the in vitro magnetic field generating element, while the magnetic auxiliary member is adjusted to another position P2' flat against the mucosa to be dissected, and the control system records the position of the in vitro magnetic dipole as a second flat position P2, the first flat position P1 and the second flat position P2 forming a plane S, the position P1' and the position P2' forming a plane S';

the control system updates the carrier coordinate system of the in vitro magnetic dipole according to the first flat position P1 and the second flat position P2: P2 as the Y axis, Z=P2×P1 as the Z axis of the coordinate system, the X-axis is determined by the right-hand rule; the control system defines the 2 rotational degrees of freedom of the in vitro magnetic dipole in the updated carrier coordinate system: the 1st' rotational degree of freedom is rotation about the Z-axis of the updated carrier coordinate system, and the 2nd' rotational degree of freedom is rotation about the rotation axis obtained by a cross product of the normal vector of the plane S and the second flat position P2;

the driving mechanism drives the in vitro magnetic dipole to rotate the 1st' rotational degree of freedom in the plane S, then the magnetic auxiliary member rotates in the plane S' of mucosa, and the magnetic auxiliary member is adjusted to the center of the plane S' of mucosa or other initial position of curling;

the driving mechanism drives the in vitro magnetic dipole to rotate the 2nd' rotational degree of freedom, then the magnetic auxiliary member starts to curl.

In another embodiment, the in vitro magnetic dipole rotates a combination of the 2 rotational degrees of freedom specifically as follows: a) change to o-x0'y0'z0 after rotating $\theta 0$ around the current z axis, and the in vitro magnetic dipole reaches position oy0'; b) change to o-x0'y1z1 after rotating $\theta 0$ around the current x0' axis, and the in vitro magnetic dipole reaches position oy1; c) change to o-x1y1'z1 after rotating $\varphi 1$ around the current z1 axis, and the in vitro magnetic dipole reaches position oy1'.

In another embodiment, the driving mechanism drives the in vitro magnetic field generating element to make the in vitro magnetic dipole rotate according to 2 rotational degrees of freedom in the following way: the carrier coordinate system of the in vitro magnetic dipole is built as o-xyz with the current position of the in vitro magnetic dipole as oy; and the base coordinate system of the driving mechanism is built as O-XYZ; according to the position change of the in vitro magnetic dipole before and after the rotation of any of the 2 rotational degrees of freedom, the spherical coordinate angle component of the in vitro magnetic dipole before and after the rotation is calculated, and the driving mechanism determines the rotation angle of the in vitro magnetic field generating element according to the angle component and drives the rotation of the in vitro magnetic field generating element.

The present invention further provides a method for controlling the auxiliary apparatus for minimally invasive surgery. The method comprises the steps of:

step S1, when the locating probe is placed at the center of the pre-cut mucosa to be dissected, the driving mechanism drives the in vitro magnetic field generating element to move; and when the magnetic field intensity detected by the locating probe reaches a peak value, the in vitro magnetic field generating element stops at its current position and does not move again;

step S2, when the in vivo device is placed on the edge of the mucosa to be dissected, the clip clips the mucosa to be dissected and the in vitro magnetic field generating element generates an in vitro magnetic field, the control system builds a carrier coordinate system O-XYZ of an in vitro magnetic dipole, and defines the 2 rotational degrees of freedom of the in vitro magnetic dipole in the carrier coordinate system as rotation about the X-axis and Z-axis, respectively; where the direction of the in vitro magnetic dipole is taken as the Y-axis direction, and the X-axis and Z-axis are the coordinate axes selected in the plane perpendicular to the Y-axis, and the X-axis, Y-axis and Z-axis conform to the right-hand rule;

step S3, the driving mechanism drives the in vitro magnetic field generating element to make the in vitro magnetic dipole rotate a combination of the 2 rotational degrees of freedom, the magnetic auxiliary member moves and/or rotates accordingly with the rotation of the in vitro magnetic field generating element, while the magnetic auxiliary member is adjusted to a position P1' flat against the mucosa to be dissected, and the control system records the position of the in vitro magnetic dipole as a first flat position P1;

the driving mechanism drives the in vitro magnetic field generating element to make the in vitro magnetic dipole rotate a combination of the 2 rotational degrees of freedom, the magnetic auxiliary member moves and/or rotates accordingly with the rotation of the in vitro magnetic field generating element, while the magnetic auxiliary member is adjusted to another position P2' flat against the mucosa to be dissected, and the control system records the position of the in vitro magnetic dipole as a second flat position P2, the first flat position P1 and the second flat position P2 forming a plane S, the position P1' and the position P2' forming a plane S';

step S4, the control system updates the carrier coordinate system of the in vitro magnetic dipole according to the first flat position P1 and the second flat position P2: P2 as the Y axis, Z=P2×P1 as the Z axis of the coordinate system, the X-axis is determined by the right-hand rule; the control system defines the 2 rotational degrees of freedom of the in vitro magnetic dipole in the updated carrier coordinate system: the 1st' rotational degree of freedom is rotation about the Z-axis of the updated carrier coordinate system, and the 2nd' rotational degree of freedom is rotation about the rotation obtained by a cross product of the normal vector of the plane S and the second flat position P2;

step S5, the driving mechanism drives the in vitro magnetic dipole to rotate the 1st' rotational degree of freedom in the plane S, and accordingly, the magnetic auxiliary member rotates in the plane S' of mucosa, and the magnetic auxiliary member is adjusted to the center of the plane S' of mucosa or other initial position of curling;

step S6, the driving mechanism drives the in vitro magnetic dipole to rotate the 2nd' rotational degree of freedom, and accordingly the magnetic auxiliary member starts to curl mucosa.

The advantages of the present disclosure include: the auxiliary apparatus for minimally invasive surgery detects the peak value of the magnetic field generated by the in vitro magnetic field generating element through a locating probe and locates the in vitro magnetic field generating element so that the in vitro magnetic field generating element is in the same vertical line with the mucosa to be dissected to ensure the maximum torque for the subsequent curling; and a precise control of the movement and/or rotation of the in vivo device by the in vitro device is achieved through a control system, so that the curling operation of the in vivo device to the mucosa to be dissected facilitates the ESD procedure.

In addition, the method for the controlling of the auxiliary apparatus can achieve the effects of easy control of the mucosa curling angle, high repeatability of operation, fast speed, high safety and reliability for the mucosa to be dissected in any spatial orientation; also, it can effectively control the magnetic auxiliary member to roll the mucosa to a proper angle, expose the new submucosal tissue, and facilitate the subsequent application of an electrotome to continue the dissection of the mucosa.

DETAILED DESCRIPTION

Figure 1:
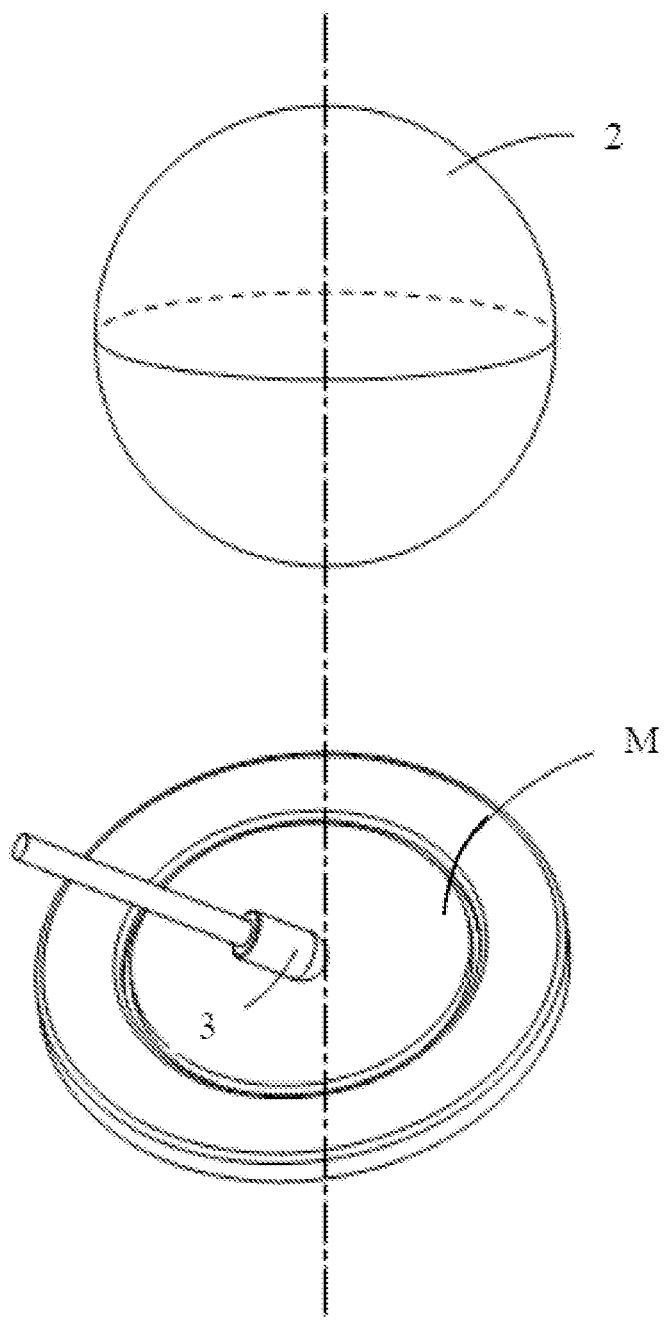
FIG. 1 depicts a locating device that works with an in vitro device to locate an in vitro magnetic field generating element in accordance with the present invention.

Reference will now be made to the drawing figures to describe the embodiments of the present disclosure in detail.

In the following description, the same drawing reference numerals are used for the same elements in different drawings.

In the present invention, the mucosa M to be dissected may be the gastrointestinal mucosa of human or animal, the gastrointestinal mucosa of in vitro tissue, the gastrointestinal mucosa corresponding to a gastrointestinal tract model, or a simulated gastrointestinal mucosa, etc.

Referring to FIGS. 1-6, the present invention provides an auxiliary apparatus for minimally invasive surgery to stretch surgery targets, comprising an in vivo device 1 disposed inside the body to stretch the mucosa M to be dissected during use, an in vitro device 2 disposed outside the body to manipulate the in vivo device 1 to move and/or rotate, a locating probe 3 that works with the in vitro device 2 to assist in locating the in vitro device 2, and a control system (not shown). The mucosa M to be dissected may be the mucosa of an in vitro tissue of animal or the mucosa on a simulated medical model, etc.

The in vitro device 2 comprises an in vitro magnetic field generating element 21 that provides a uniform magnetic field, and a driving mechanism 22 that drives the in vitro magnetic field generating element 21 to move and/or rotate. The uniform magnetic field may be understood as a uniform magnetic field, an approximately uniform magnetic field, a magnetic field in part of the space as a uniform magnetic field. In the present invention, the in vitro magnetic field generating element 21 may be a spherical permanent magnet, or a Helmholtz coil, or a cylindrical permanent magnet, and the in vitro magnetic field generating element 21 may be controlled by a human or mechanical device to move and rotate so as to be able to generate a uniform rotating magnetic field in any direction. For the convenience of describing the direction of movement and rotation of the in vitro magnetic field generating element 21, the in vitro magnetic field generating element 21 is referred to as an in vitro magnetic dipole when generating an in vitro magnetic field.

In one embodiment, the driving mechanism 22 comprises a motor (not shown) controlled by the control system, a 3-10 axis linkage robotic arm or a two-degree-of-freedom turntable driven by the motor to move and/or rotate the in vitro magnetic field generating element 21. The control system receives commands through a human-machine interface and then controls the movement of the robotic arm or the two-degree-of-freedom turntable through a motor to control the in vitro magnetic field generating element 21 to move and/or rotate in three dimensions in space.

The 3-10 axis linkage robotic arm refers to any mechanical device that can fix the in vitro magnetic field generating element 21 and can drive the in vitro magnetic field generating element 21 to move and/or rotate in three dimensions in the out-of-body space, and its specific structure is not limited. Regarding how the in vitro device 2 controls the in vitro magnetic field generating element 21 to move in three dimensions and/or rotate in two dimensions in space through a driving mechanism, please refer to Chinese Patent No. 201310136094.0.

The in vivo device 1 comprises a magnetic auxiliary member 11 and a clip 12 connected to the magnetic auxiliary member 11. The clip 12 is used to fix the magnetic auxiliary member 11 to the mucosa to be stretched. After the magnetic auxiliary member 11 is fixed to the clip 12, and the clip 12 is fixed to the surgery target to be stretched, the magnetic auxiliary member 11 moves and/or rotates accordingly to changes in the direction of the magnetic field of the in vitro magnetic field generating element 21, which in turn causes the surgery target to move at a controlled speed and/or rotate at a controlled angle to wrap around the in vivo device 1 to enlarge the visual field of endoscopic submucosal dissection (ESD) surgery.

The clip 12 is usually a medical hemostatic clip, a hemostatic forceps or a titanium clip, and is used to take hold of the surgery target. The clip is usually made of medical materials, such as pure titanium or titanium alloy.

The structure and shape of the magnetic auxiliary member 11 are not limited, as long as it can move and/or rotate in response to changes in the in vitro magnetic field. Preferably, the magnetic auxiliary member 11 is constructed to be cylindrical in shape to facilitate control of its movement and/or rotation. In the embodiment, the magnetic auxiliary member 11 comprises a first limit member, a second limit member and at least one magnetic cylinder disposed between the first limit member and the second limit member, and a connective thread connecting the first limit member and the at least one magnetic cylinder to the second limit member. Specifically, the first limit member comprises a first through hole penetrating through the first limiting member, the second limit member comprises a second through hole penetrating through the second limiting member, the magnetic cylinder comprises a third through hole, and the connective thread passes through the first through hole, the third through hole and the second through hole to join the first limit member, at least one magnetic cylinder and the second limit member together. The first limit member and the second limit member can be constructed of materials such as plastic, stainless steel, or magnet.

The magnetic cylinder is a functional part of the magnetic auxiliary member 11 and may be constructed of a permanent magnetic material such as ferrite, neodymium iron boron, samarium cobalt or alnico. Alternatively, the surface of the magnetic cylinder may be coated with a biocompatible film. The biocompatible film is titanium, titanium nitride, titanium oxide, nickel, nickel oxide, parelin or fluoride, etc. The fluoride is preferably polytetrafluoroethylene.

It can be appreciated by those skilled in the art that "at least one magnetic cylinder" can be a single magnetic cylinder, which is applicable to situations where the surgical space is confined. In the case where the total size of the at least one magnetic cylinder and the magnetic force provided by the in vitro device 2 remain unchanged, the curling torque of only one magnetic cylinder is greater than the curling torque of a plurality of magnetic cylinders. The "at least one magnetic cylinder" can also be a plurality of magnetic cylinders; a plurality of magnetic cylinders is arranged into a large magnet to ensure that the magnetic auxiliary member 11 can pass smoothly through the instrument channel despite a serious bending of the endoscope body to meet the clinical needs of ESD surgery. The number of the magnetic cylinders is determined by the size of the surgery target to be stretched, the larger the surgery target, the greater the number of the magnetic cylinders, and vice versa. The magnetic cylinder is axially polarized, and all the magnetic cylinders have the same direction of polarization. Alternatively, the magnetic tube may also be radially polarized. Then, the magnetic auxiliary member 11 comprises odd numbered magnetic cylinders, which are connected to each other side by side under magnetic force by threading of the connective thread, with two adjacent magnetic cylinders polarized in opposite directions.

The first limit member, the second limit member and the connective thread are used to connect at least one magnetic cylinder into a magnetic whole. The connective thread may be selected from, but not limited to, nylon thread, polypropylene (Proline) and other medical sutures, and one end of the connective thread is in the form of a knot, adjustable diameter ring, etc., which may be fixed to the clip 12. For the specific fixing method, refer to Chinese patent application No. 201510661964.5.

The locating probe 3 comprises a magnetic field sensor for detecting the magnetic field intensity of the in vitro magnetic field generating element 21. The magnetic field sensor may be a magnetic field sensor based on magnetoresistive effect or may be a Hall sensor. The Hall sensor is used as an example to illustrate the method of using the locating probe 3. As shown in FIG. 1, the locating probe 3 is placed in the center of the pre-cut mucosa, and the driving mechanism 22 drives the in vitro magnetic field generating element 21 to move. When the Hall sensor detects the maximum intensity of the magnetic field generated by the in vitro magnetic field generating element 21, the in vitro magnetic field generating element 21 stops moving. Locating the in vitro magnetic field generating element 21 by the locating probe 3 can not only ensure the maximum torque of the in vitro magnetic field generating element 21 for the control of at least one magnetic cylinder in the subsequent operation, but can also work with the in vivo device 1 for the magnetic stretching of the mucosa in any spatial position, with easy control of the stretching angle, high repeatability of the operation, fast speed, high safety and reliability.

Both the driving mechanism 22 and the locating probe 3 directly or indirectly communicate with the control system for the transmission of signals. One indirect communication method is to provide signals to the control system through a human-machine interface.

The auxiliary apparatus for minimally invasive surgery further comprises a support tube to assist in the delivery of the locating probe 3 and the in vivo device 1 into the body. During use, the locating probe 3 and the in vivo device 1 reach through the support tube to the mucosa to be dissected.

The in vitro device 2 and the locating probe 3 are configured such that: referring to FIG. 1, when the locating probe 3 is placed at the center of the pre-cut mucosa to be dissected, the driving mechanism 22 drives the in vitro magnetic field generating element 21 to move, and when the magnetic field intensity detected by the locating probe 3 reaches its peak value, the in vitro magnetic field generating element 21 stops at its current position and does not move again. The driving mechanism 22 controls the in vitro magnetic field generating element 21 such that: the control system controls the motor to start, and the motor drives the robotic arm to move the in vitro magnetic field generating element 21 until the magnetic field intensity detected by the locating probe 3 reaches the peak value.

Specifically, after the mucosa is pre-cut, the locating probe 3 is released to the surgery target through the support tube, and is placed against the center of the precut mucosa M to be dissected, and the locating probe 3 is kept still. A command is sent to the control system through the human-machine interface, and the control system controls the motor to start, so that the robotic arm drives the in vitro magnetic field generating element 21 to move. When the magnetic field intensity detected by the locating probe 3 reaches the peak value, the in vitro magnetic field generating element 21 stops moving. At this point, the in vitro magnetic field generating element 21 is in the same vertical line with the mucosa to be dissected to ensure the maximum torque for the subsequent curling. After the locating of the in vitro magnetic field generating element 21 is completed, the locating probe 3 can be removed through the support tube.

Figure 2:
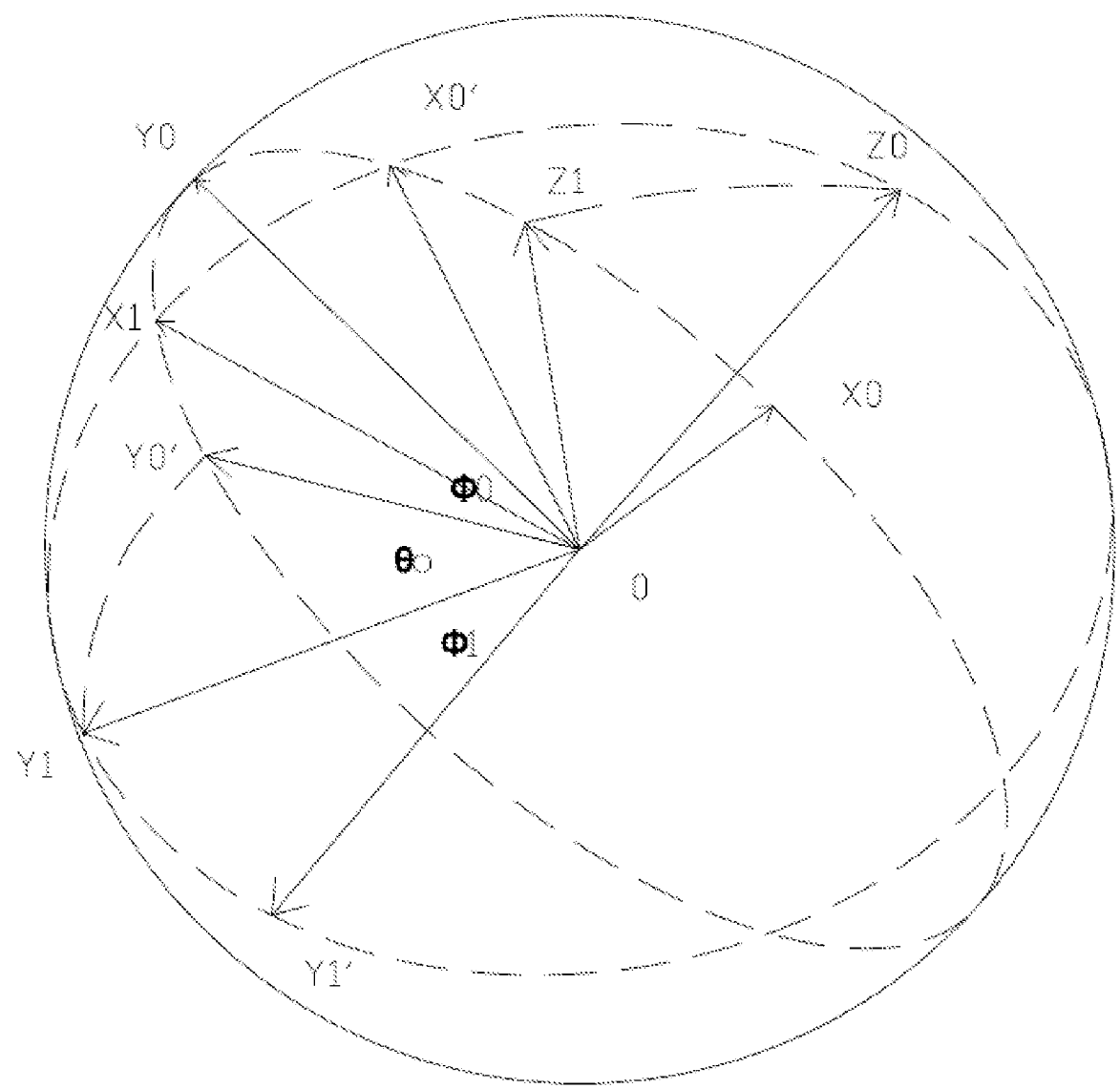
FIG. 2 depicts the 2 rotational degrees of freedom of an in vitro magnetic dipole in accordance with the present invention.

The in vitro device 2 and the in vivo device 1 are configured such that: referring to FIG. 2, when the in vivo device 1 is placed on the edge of the mucosa to be dissected, the clip 12 clips the mucosa M to be dissected, and the in vitro magnetic field generating element 21 generates an in vitro magnetic field; the control system defines 2 rotational degrees of freedom of an in vitro magnetic dipole according to a default trajectory generator and the driving mechanism 22 drives the in vitro magnetic field generating element 21 so that the in vitro magnetic dipole rotates a combination of the 2 rotational degrees of freedom, and the magnetic auxiliary member 11 moves and/or rotates accordingly with the rotation of the in vitro magnetic field generating element 21.

The default trajectory generator is configured to: build in the control system a carrier coordinate system O-XYZ of the in vitro magnetic dipole, where the direction of the in vitro magnetic dipole is taken as the Y-axis direction, the X-axis and Z-axis are the coordinate axes selected in the plane perpendicular to the Y-axis, and the X-axis, Y-axis and Z-axis conform to the right-hand rule; define the 2 rotational degrees of freedom of the in vitro magnetic dipole in the carrier coordinate system as rotation about the X-axis and Z-axis, respectively. It can be appreciated by those skilled in the art that regardless of the orientation of the in vitro magnetic dipole on the spherical plane, the direction of the in vitro magnetic dipole always coincides with the Y-axis in the carrier coordinate system, and the two rotational degrees of freedom of the in vitro magnetic dipole defined by the default trajectory generator are rotation about X-axis and Z-axis respectively; that is, the carrier coordinate system can be adjusted accordingly when the in vitro magnetic dipole is in different orientations.

Figure 3:
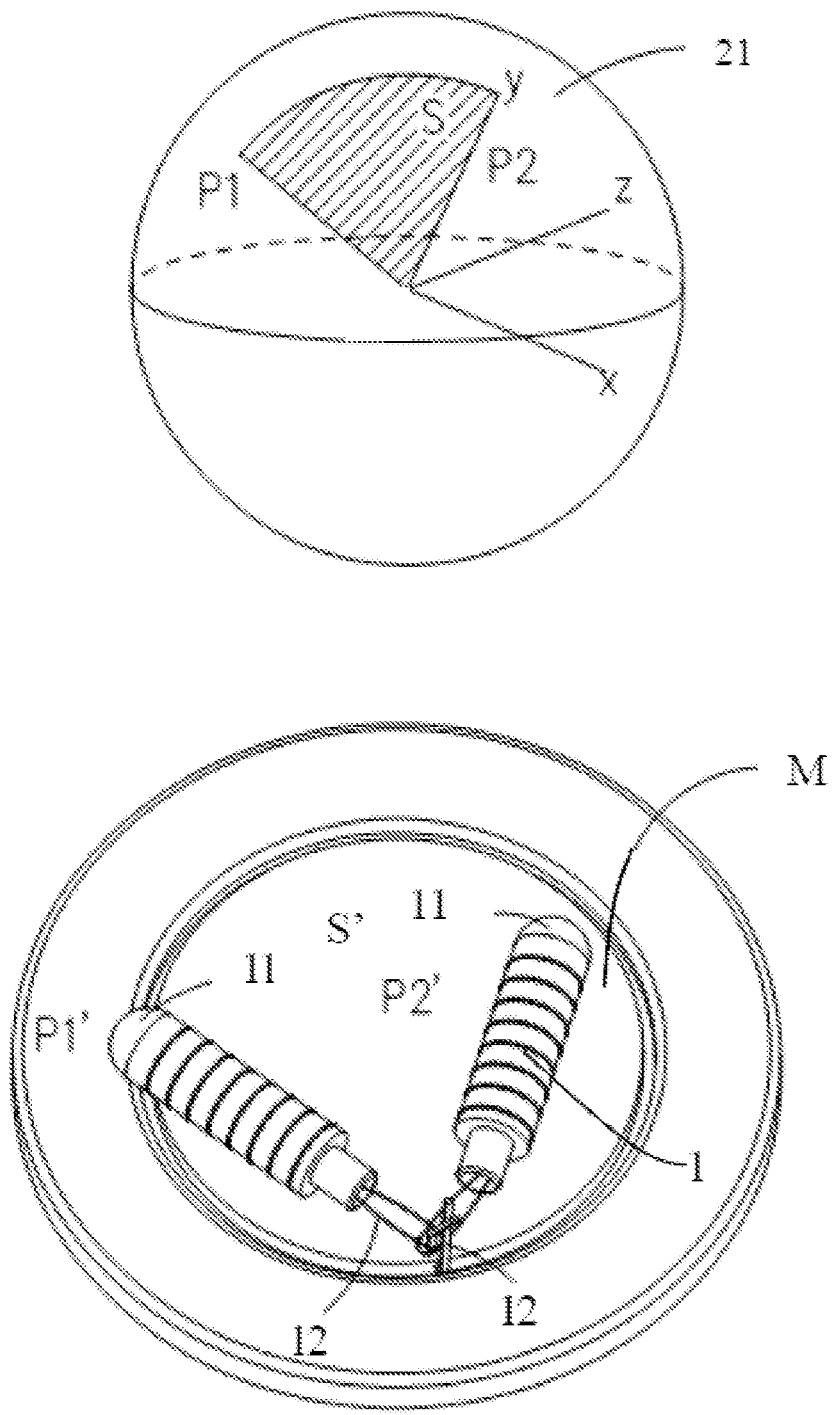
FIG. 3 depicts the controlling of the in vitro magnetic dipole to rotate a combination of 2 degrees of freedom respectively to make a magnetic auxiliary member flat against the surface of the mucosa to be dissected in accordance with the present invention.

Referring to FIG. 3, the driving mechanism 22 drives the in vitro magnetic field generating element 21 to make the in vitro magnetic dipole rotate a combination of the 2 rotational degrees of freedom, the magnetic auxiliary member 11 moves and/or rotates accordingly with the rotation of the in vitro magnetic field generating element 21, while the magnetic auxiliary member 11 is adjusted to a position P1' flat against the mucosa M to be dissected in combination with images captured by the endoscope, and the control system records the position of the in vitro magnetic dipole as a first flat position P1.

The driving mechanism 22 drives the in vitro magnetic field generating element 21 to make the in vitro magnetic dipole rotate a combination of the 2 rotational degrees of freedom, the magnetic auxiliary member 11 moves and/or rotates accordingly with the rotation of the in vitro magnetic field generating element 21, while the magnetic auxiliary member 11 is adjusted to another position P2' flat against the mucosa M to be dissected in combination with images captured by the endoscope, and the control system records the position of the in vitro magnetic dipole as a second flat position P2.

Where, "the in vitro magnetic dipole rotates a combination of the two rotational degrees of freedom" is depicted in detail in FIG. 2. In an example, the 1st rotational degree of freedom that is a rotation about the Z axis and the 2nd rotational degree of freedom is a rotation about the X axis. Referring to FIG. 2, the method of rotation of the in vitro magnetic dipole that rotates a combination of the 2 rotational degrees of freedom is illustrated:

change to o-x0'y0'z0 after rotating φ0 around the current z0 axis (rotating the 1st rotational degree of freedom), and the in vitro magnetic dipole reaches position oy0'; b) change to o-x0'y1z1 after rotating θ0 around the current x0' axis (rotating the 2nd rotational degree of freedom), and the in vitro magnetic dipole reaches position oy1; c) change to o-x1y1'z1 after rotating q1 around the current z1 axis (rotating the 1st rotational degree of freedom), and the in vitro magnetic dipole reaches position oy1'.

Figure 4:
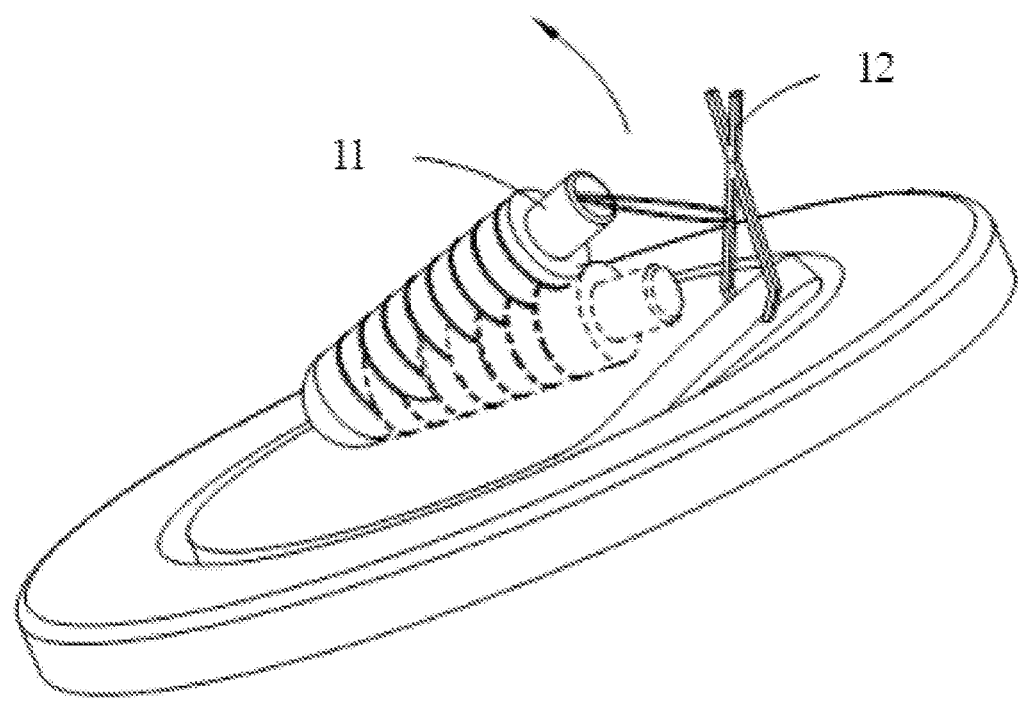
FIG. 4 depicts the guiding of the magnetic auxiliary member to the center of the mucosa to be dissected as the starting point for curling by rotating the 1st' rotational degree of freedom of the in vitro magnetic dipole, and the controlling of the magnetic auxiliary member to curl the mucosa to be dissected by rotating the 2nd' rotational degree of freedom of the in vitro magnetic dipole.
Figure 5:
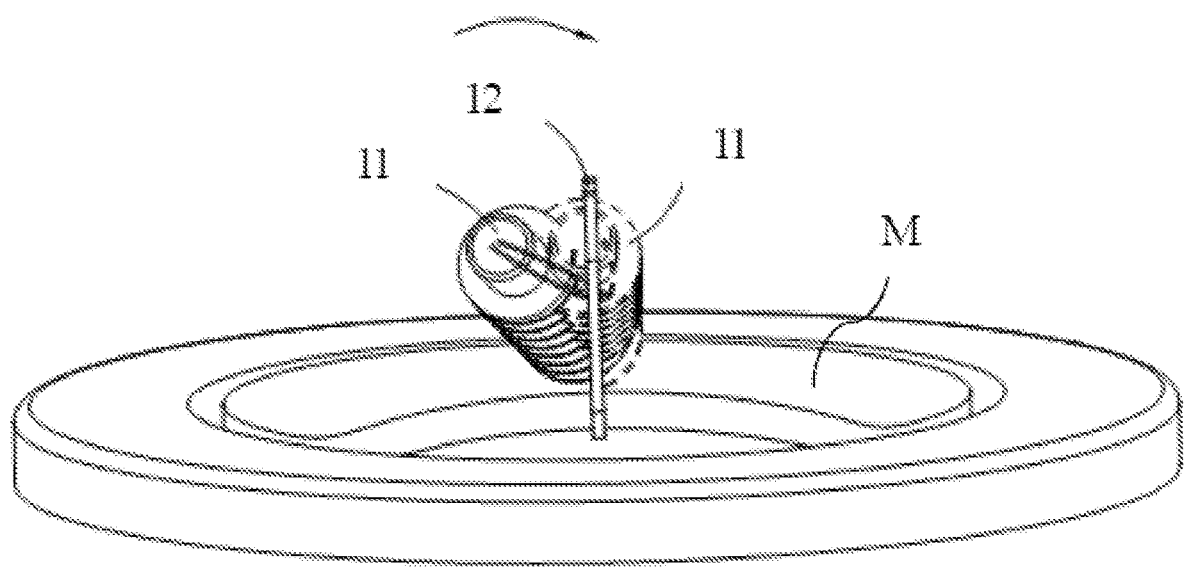
FIG. 5 depicts the adjusting of the magnetic auxiliary member to adjust the direction of stretching by rotating the 1st' rotational degree of freedom of the in vitro magnetic dipole when the magnetic auxiliary member is deflected during the flipping of the mucosa to be dissected.

Referring to FIGS. 3-5, after the in vitro magnetic dipole rotates a combination of the 2 rotational degrees of freedom, and the control system records the first flat position P1 and the second flat position P2 of the in vitro magnetic dipole, the control system updates the trajectory generator according to the first flat position P1 and the second flat position P2, and the control system enters a state of mucosa curling, that is, the magnetic auxiliary member 11 starts to curl according to the updated carrier coordinate system. A command is sent to the control system through the human-machine interface, and the control system updates the carrier coordinate system of the in vitro magnetic dipole: P2 is used as the Y-axis, Z=P2×P1 is used as the Z-axis of the coordinate system, and the X-axis is determined by the right-hand rule.

The 2 rotational degrees of freedom of the in vitro magnetic dipole are defined according to the updated trajectory generator: the 1st' rotational degree of freedom is rotation about the Z-axis of the updated carrier coordinate system, that is, the in vitro magnetic dipole rotates in the plane S formed by the first flat position P1 and the second flat position P2, and accordingly the magnetic auxiliary member 11 rotates in the plane S' formed by the two flat positions P1' and P2' of the mucosa M to be dissected; the 2nd' rotational degree of freedom is rotation about the rotation axis obtained by a cross product of the normal vector of the plane S and the second flat position P2.

The in vitro magnetic dipole rotates in the plane S when it rotates the 1st' rotational degree of freedom, and accordingly the magnetic auxiliary member 11 rotates in the plane S' of the mucosa, where are ensured by the following principle: $\Omega=H\cdot\omega$. where, $\Omega$ is the direction of rotation of the in vitro magnetic dipole, $\omega$ is the direction of rotation of the magnetic auxiliary member 11, and H is the orientation matrix. Since the relative spatial position of the in vitro magnetic field generating element 21 and the magnetic auxiliary member 11 is constant, H is a constant, so when the in vitro magnetic dipole rotates in a certain plane, the magnetic auxiliary member 11 rotates in the corresponding plane.

Referring to FIG. 4, the control system controls the driving mechanism to drive the in vitro magnetic dipole to rotate the 1st' rotational degree of freedom in the plane S. Accordingly, the magnetic auxiliary member 11 rotates in the plane S' of the mucosa. In conjunction with the endoscopic images, the magnetic auxiliary member 11 is adjusted to the center of the mucosa plane S' or to the initial position of curling as deemed more appropriate by the ESD surgeon, as the initial position for the subsequent curling.

The control system controls the driving mechanism to drive the in vitro magnetic dipole to rotate the 2nd' rotational degree of freedom so that the in vitro magnetic dipole rotates around the X-axis of the updated carrier coordinate system. Accordingly, the magnetic auxiliary member 11 starts to curl, and the mucosa to be dissected starts to wrap the in vivo device 1. In combination with the endoscopic images, the magnetic auxiliary member 11 is controlled to curl at a suitable angle so that the submucosal tissue is exposed to facilitate the surgeon to apply an electrotome to start excision and dissect the mucosa.

Referring to FIG. 5, in the curling process, if the magnetic auxiliary member 11 has a deflection caused by the sliding between the magnetic auxiliary member 11 and the mucosa or between the magnetic auxiliary member 11 and the anchoring point, the deflection can be adjusted by rotating the 1st' rotation degree of freedom to adjust the stretching direction of the magnetic auxiliary member 11, and after the adjustment, the mucosa is curled in the new stretching direction by rotating the 2nd' rotational degree of freedom.

According to the needs of a surgeon, it is selectable to rotate the 1st' rotational degree of freedom to adjust the stretching direction of the magnetic auxiliary member 11 and rotate the 2nd' rotational degree of freedom to control the degree of mucosa curling. For one thing, the effects of easy control of the mucosa curling angle, high repeatability of operation, fast speed, high safety and reliability for the mucosa M to be dissected in any spatial orientation can be achieved. For another, it can effectively control the magnetic auxiliary member to roll the mucosa to a proper angle, expose the new submucosal tissue, and facilitate the subsequent application of an electrotome to continue the dissection of the mucosa.

In addition, since the rotation axes of the 1st' rotational degree of freedom and the 2nd' rotational degree of freedom are arbitrary vectors during the motion of the in vitro magnetic dipole, it is necessary to realize that the in vitro magnetic dipole can rotate around any axis on the spherical plane to which the in vitro magnetic field generating element 21 belongs.

The driving mechanism 22 drives the in vitro magnetic field generating element 21 to make the in vitro magnetic dipole rotate according to 2 rotational degrees of freedom in the following way: the carrier coordinate system of the in vitro magnetic dipole is built as o-xyz with the current position of the in vitro magnetic dipole as oy; and the base coordinate system of the driving mechanism 22 is built as O-XYZ; according to the position change of the in vitro magnetic dipole before and after the rotation of any of the 2 rotational degrees of freedom, the spherical coordinate angle component of the in vitro magnetic dipole before and after the rotation is calculated, and the driving mechanism 22 determines the rotation angle of the in vitro magnetic field generating element 21 according to the angle component and drives the rotation of the in vitro magnetic field generating element 21.

Figure 6:
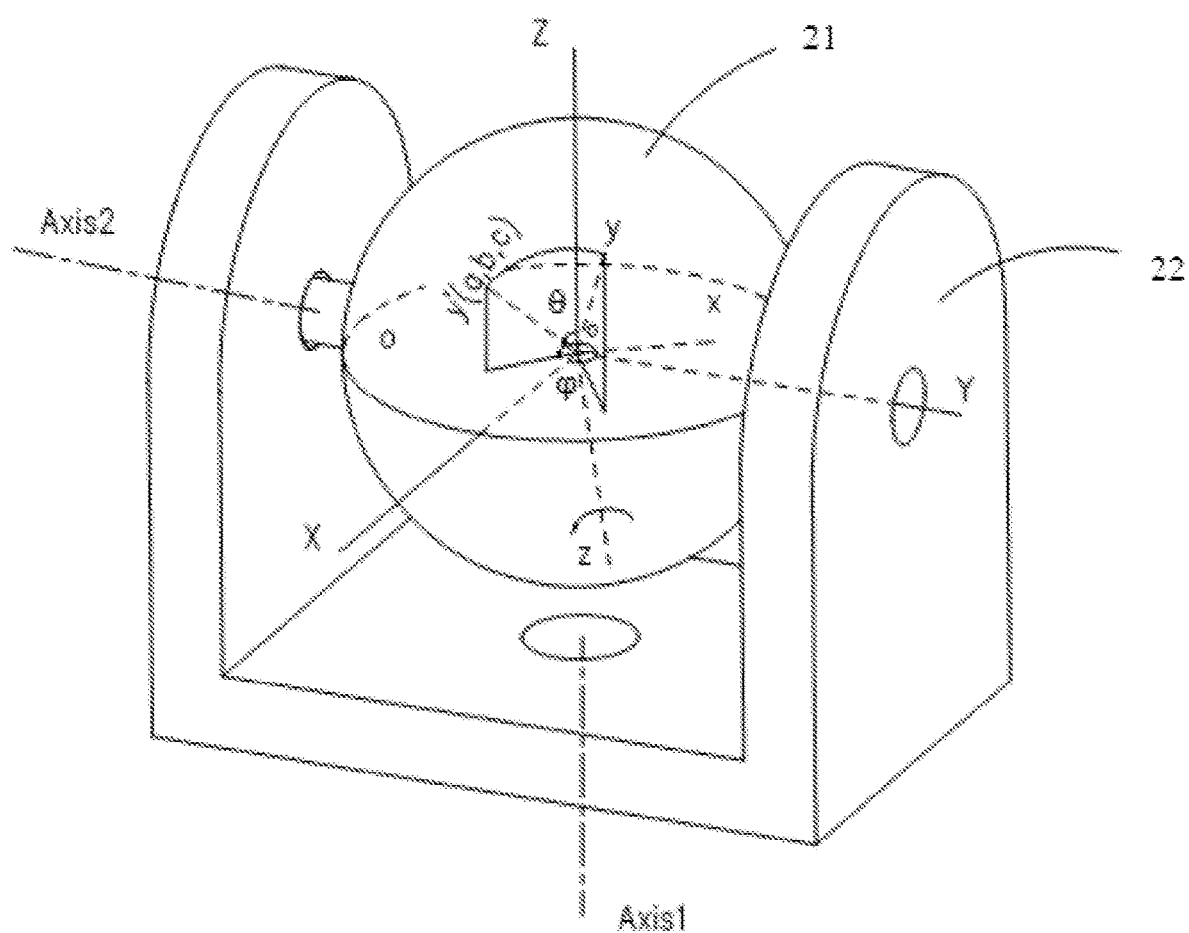
FIG. 6 depicts the principle of rotating the in vitro magnetic dipole around any axis in space using a two-degree-of-freedom turntable.

In the embodiment, referring to FIG. 6, a two-degree-of-freedom turntable is used to realize the rotation of an in vitro magnetic dipole around any axis in space, as an example. The principle is as follows:

The current position of the in vitro magnetic dipole is oy, the carrier coordinate system of the in vitro magnetic dipole is o-xyz, the base coordinate system of the two-degree-of-freedom turntable is O-XYZ, the 1st' rotational degree of freedom is rotation about the z-axis of the carrier coordinate system (Rotz), and the 2nd' rotational degree of freedom is rotation about the x-axis of the carrier coordinate system (Rotx). If the command is sent to the control system for Rotz rotation angle: A=<oy, oy'>, that is, the desired position of the in vitro magnetic dipole is the position oy' on the spherical plane—y' (a, b, c). The angle component ($\theta$, $\varphi$) of the oy' spherical coordinate is calculated, which is the quantity of Axis1 and Axis2 angular positions of the two-degree-of-freedom turntable. For the case of rotating the 2nd' rotational degree of freedom about the x-axis of the carrier coordinate system, the calculation method is the same as above and is be described here.

The present invention further provides a method for the controlling of the auxiliary apparatus for minimally invasive surgery (MIS), comprising the steps of:

step S1, when the locating probe 3 is placed at the center of the pre-cut mucosa M to be dissected, the driving mechanism 22 drives the in vitro magnetic field generating element 21 to move; and when the magnetic field intensity detected by the locating probe 3 reaches a peak value, the in vitro magnetic field generating element 21 stops at its current position and does not move again;

step S2, when the in vivo device 1 is placed on the edge of the mucosa M to be dissected, the clip 12 clips the mucosa M to be dissected and the in vitro magnetic field generating element 21 generates an in vitro magnetic field, the control system builds a carrier coordinate system O-XYZ of the in vitro magnetic dipole, and defines the 2 rotational degrees of freedom of the in vitro magnetic dipole in the carrier coordinate system as rotation about the X-axis and Z-axis, respectively; where the direction of the in vitro magnetic dipole is taken as the Y-axis direction, and the X-axis and Z-axis are the coordinate axes selected in the plane perpendicular to the Y-axis, and the X-axis, Y-axis and Z-axis conform to the right-hand rule;

step S3, the driving mechanism 22 drives the in vitro magnetic field generating element 21 to make the in vitro magnetic dipole rotate a combination of the 2 rotational degrees of freedom, the magnetic auxiliary member 11 moves and/or rotates accordingly with the rotation of the in vitro magnetic field generating element 21, while the magnetic auxiliary member 11 is adjusted to a position P1' flat against the mucosa M to be dissected, and the control system records the position of the in vitro magnetic dipole as a first flat position P1;

the driving mechanism 22 drives the in vitro magnetic field generating element 21 to make the in vitro magnetic dipole rotate a combination of the 2 rotational degrees of freedom, the magnetic auxiliary member 11 moves and/or rotates accordingly with the rotation of the in vitro magnetic field generating element 21, while the magnetic auxiliary member 11 is adjusted to another position P2' flat against the mucosa M to be dissected, and the control system records the position of the in vitro magnetic dipole as a second flat position P2, the first flat position P1 and the second flat position P2 forming a plane S, the position P1' and the position P2' forming a plane S';

step S4, the control system updates the carrier coordinate system of the in vitro magnetic dipole according to the first flat position P1 and the second flat position P2: P2 as the Y axis, $Z=P2\times P1$ as the Z axis of the coordinate system, the X-axis is determined by the right-hand rule; the control system defines the 2 rotational degrees of freedom of the in vitro magnetic dipole in the updated carrier coordinate system: the 1st' rotational degree of freedom is rotation about the Z-axis of the updated carrier coordinate system, and the 2nd' rotational degree of freedom is rotation about the rotation axis obtained by a cross product of the normal vector of the plane S and the second flat position P2;

step S5, the control system controls the driving mechanism to drive the in vitro magnetic dipole to rotate the 1st' rotational degree of freedom in the plane S, and accordingly, the magnetic auxiliary member 11 rotates in the plane S' of mucosa, and the magnetic auxiliary member 11 is adjusted to the center of the plane S' of mucosa or other initial position of curling;

step S6, the control system controls the driving mechanism to drive the in vitro magnetic dipole to rotate the 2nd' rotational degree of freedom, and accordingly the magnetic auxiliary member 11 starts to curl mucosa.

The driving mechanism 22 drives the in vitro magnetic field generating element 21 to make the in vitro magnetic dipole rotate according to 2 rotational degrees of freedom in the following way: the carrier coordinate system of the in vitro magnetic dipole is built as o-xyz with the current position of the in vitro magnetic dipole as oy; and the base coordinate system of the driving mechanism 22 is built as O-XYZ; according to the position change of the in vitro magnetic dipole before and after the rotation of any of the 2 rotational degrees of freedom, the spherical coordinate angle component of the in vitro magnetic dipole before and after the rotation is calculated, and the driving mechanism 22 determines the rotation angle of the in vitro magnetic field generating element 21 according to the angle component and drives the rotation of the in vitro magnetic field generating element 21.

In addition, other specific steps in the auxiliary apparatus for MIS can be used in the method of controlling the auxiliary apparatus for MIS and is not described here.

In summary, the auxiliary apparatus for MIS detects the peak value of the magnetic field generated by the in vitro magnetic field generating element 21 through a locating probe 3 and locates the in vitro magnetic field generating element 21 so that the in vitro magnetic field generating element 21 is in the same vertical line with the mucosa to be dissected to ensure the maximum torque for the subsequent curling; and a precise control of the movement and/or rotation of the in vivo device 1 by the in vitro device 2 is achieved through a control system, so that the curling operation of the in vivo device to the mucosa to be dissected facilitates the ESD procedure.

In addition, the method for the controlling of the auxiliary apparatus can achieve the effects of easy control of the mucosa curling angle, high repeatability of operation, fast speed, high safety and reliability for the mucosa M to be dissected in any spatial orientation; also, it can effectively control the magnetic auxiliary member 11 to roll the mucosa to a proper angle, expose the new submucosal tissue, and facilitate the subsequent application of an electrotome to continue the dissection of the mucosa.

It is to be understood, however, that even though numerous characteristics and advantages of preferred and exemplary embodiments have been set out in the foregoing description, together with details of the structures and functions of the embodiments, the disclosure is illustrative only; and that changes may be made in detail within the principles of the present disclosure to the full extent indicated by the broadest general meaning of the terms in which the appended claims are expressed.

What is claimed is:

1. An auxiliary apparatus for minimally invasive surgery, comprising:
   an in vitro device, comprised of an in vitro magnetic field generating element that provides a magnetic field for rotating a magnetic auxiliary member, and a driving mechanism that drives the in vitro magnetic field generating element to move and/or rotate;
   an in vivo device, comprised of the magnetic auxiliary member and a clip connected to the magnetic auxiliary member;
   a locating probe, comprised of a magnetic field sensor for detecting a magnetic field intensity of the in vitro magnetic field generating element; and a control system;
wherein both the driving mechanism and the locating probe directly or indirectly communicate with the control system;
wherein the in vitro device and the locating probe are configured in a manner that: the driving mechanism drives the in vitro magnetic field generating element to move while the locating probe is placed at the center of the pre-cut mucosa to be dissected; and the in vitro magnetic field generating element stops at its current position and does not move again based upon the magnetic field intensity detected by the locating probe reaching a peak value, in a manner that the in vitro magnetic field generating element is in the same vertical line with the mucosa to be dissected, ensuring the maximum torque for the subsequent curling operation of the in vivo device with respect to the mucosa to be dissected.

2. The auxiliary apparatus of claim 1, wherein the driving mechanism comprises a motor controlled by the control system, a robotic arm or a two-degree-of-freedom turntable driven by the motor to move and/or rotate the in vitro magnetic field generating element.

3. The auxiliary apparatus of claim 1, wherein the magnetic auxiliary member comprises a first limit member, a second limit member and at least one magnetic cylinder disposed between the first limit member and the second limit member, and a connective thread, wherein the first limit member comprises a first through hole, the second limit member comprises a second through hole, the magnetic cylinder comprises a third through hole, and the connective thread passes through the first through hole, the third through hole and the second through hole to join the first limit member, at least one magnetic cylinder and the second limit member together.

4. The auxiliary apparatus of claim 1, wherein the magnetic field sensor is a magnetic field sensor based on magnetoresistive effect, or a Hall sensor.

5. The auxiliary apparatus of claim 1, wherein the in vitro device and the in vivo device are configured in a manner that:
upon the in vivo device is being placed on the edge of the mucosa to be dissected, the clip clips the mucosa to be dissected, and the in vitro magnetic field generating element generates an in vitro magnetic field; the control system defines 2 rotational degrees of freedom of an in vitro magnetic dipole according to a default trajectory generator and the driving mechanism drives the in vitro magnetic field generating element in a manner that the in vitro magnetic dipole rotates a combination of the 2 rotational degrees of freedom, and the magnetic auxiliary member moves and/or rotates accordingly with the rotation of the in vitro magnetic field generating element.

6. The auxiliary apparatus of claim 5, wherein the default trajectory generator is configured to:
build in the control system a carrier coordinate system O-XYZ of the in vitro magnetic dipole, and define the 2 rotational degrees of freedom of the in vitro magnetic dipole in the carrier coordinate system as rotation about the X-axis and Z-axis, respectively; where the direction of the in vitro magnetic dipole is taken as the Y-axis direction, and the X-axis and Z-axis are the coordinate axes selected in the plane perpendicular to the Y-axis, and the X-axis, Y-axis and Z-axis conform to the right-hand rule.

7. The auxiliary apparatus of claim 5, wherein the control system is configured in a manner that:
after the in vitro magnetic dipole rotates a combination of the 2 rotational degrees of freedom, and the control system records the first flat position P1 and the second flat position P2 of the in vitro magnetic dipole, the control system updates the trajectory generator according to the first flat position P1 and the second flat position P2, and the control system enters a state of mucosa curling.

8. The auxiliary apparatus of claim 6, wherein the in vitro magnetic dipole rotates a combination of the 2 rotational degrees of freedom specifically as follows: a) change to o-x0'y0'z0 after rotating $\varphi 0$ around the current z0 axis, and the in vitro magnetic dipole reaches position oy0'; b) change to o-x0'y1z1 after rotating $\theta 0$ around the current x0' axis, and the in vitro magnetic dipole reaches position oy1; c) change to o-x1y1'z1 after rotating $\varphi 1$ around the current z1 axis, and the in vitro magnetic dipole reaches position oy1'.

9. The auxiliary apparatus of claim 5, wherein the driving mechanism drives the in vitro magnetic field generating element to make the in vitro magnetic dipole rotate according to 2 rotational degrees of freedom in the following way: the carrier coordinate system of the in vitro magnetic dipole is built as o-xyz with the current position of the in vitro magnetic dipole as oy; and the base coordinate system of the driving mechanism is built as O-XYZ; according to the position change of the in vitro magnetic dipole before and after the rotation of any of the 2 rotational degrees of freedom, the spherical coordinate angle component of the in vitro magnetic dipole before and after the rotation is calculated, and the driving mechanism determines the rotation angle of the in vitro magnetic field generating element according to the angle component and drives the rotation of the in vitro magnetic field generating element.

10. The auxiliary apparatus of claim 1, wherein the in vitro device and the in vivo device are configured in a manner that:
the driving mechanism drives the in vitro magnetic field generating element to rotate, the magnetic auxiliary member moves and/or rotates accordingly with the rotation of the in vitro magnetic field generating element, while the magnetic auxiliary member is adjusted to a position P1' flat against the mucosa to be dissected, and the control system records the position of an in vitro magnetic dipole as a first flat position P1;
the driving mechanism drives the in vitro magnetic field generating element to rotate, the magnetic auxiliary member moves and/or rotates accordingly with the rotation of the in vitro magnetic field generating element, while the magnetic auxiliary member is adjusted to another position P2' flat against the mucosa to be dissected, and the control system records the position of the in vitro magnetic dipole as a second flat position P2, the first flat position P1 and the second flat position P2 forming a plane S, the position P1' and the position P2' forming a plane S';
the control system defines the 2 rotational degrees of freedom for the rotation of the in vitro magnetic dipole as follows: the 1st' rotational degree of freedom is rotation in the plane S and the 2nd' rotational degree of freedom is rotation about the rotation axis obtained by a cross product of the normal vector of the plane S and the second flat position P2;
the driving mechanism drives the in vitro magnetic dipole to rotate the 1st' rotational degree of freedom, then the magnetic auxiliary member rotates in the plane S' of mucosa, and the magnetic auxiliary member is adjusted to the center of the plane S' of mucosa or other initial position of curling;

the driving mechanism drives the in vitro magnetic dipole to rotate the 2nd' rotational degree of freedom, then the magnetic auxiliary member starts to curl.

11. The auxiliary apparatus of claim 1, wherein the in vitro device and the in vivo device are configured in a manner that:

the driving mechanism drives the in vitro magnetic field generating element to make the in vitro magnetic dipole rotate a combination of the 2 rotational degrees of freedom, the magnetic auxiliary member moves and/or rotates accordingly with the rotation of the in vitro magnetic field generating element, while the magnetic auxiliary member is adjusted to a position P1' flat against the mucosa to be dissected, and the control system records the position of the in vitro magnetic dipole as a first flat position P1;

the driving mechanism drives the in vitro magnetic field generating element to make the in vitro magnetic dipole rotate a combination of the 2 rotational degrees of freedom, the magnetic auxiliary member moves and/or rotates accordingly with the rotation of the in vitro magnetic field generating element, while the magnetic auxiliary member is adjusted to another position P2' flat against the mucosa to be dissected, and the control system records the position of the in vitro magnetic dipole as a second flat position P2, the first flat position P1 and the second flat position P2 forming a plane S, the position P1' and the position P2' forming a plane S';

the control system updates the carrier coordinate system of the in vitro magnetic dipole according to the first flat position P1 and the second flat position P2: P2 as the Y axis, Z=P2×P1 as the Z axis of the coordinate system, the X-axis is determined by the right-hand rule; the control system defines the 2 rotational degrees of freedom of the in vitro magnetic dipole in the updated carrier coordinate system: the 1st' rotational degree of freedom is rotation about the Z-axis of the updated carrier coordinate system, and the 2nd' rotational degree of freedom is rotation about the rotation axis obtained by a cross product of the normal vector of the plane S and the second flat position P2;

the driving mechanism drives the in vitro magnetic dipole to rotate the 1st' rotational degree of freedom in the plane S, then the magnetic auxiliary member rotates in the plane S' of mucosa, and the magnetic auxiliary member is adjusted to the center of the plane S' of mucosa or other initial position of curling; and the driving mechanism drives the in vitro magnetic dipole to rotate the 2nd' rotational degree of freedom, then the magnetic auxiliary member starts to curl.

12. A method for controlling auxiliary apparatus for minimally invasive surgery of claim 1, comprising the steps of:

step S1, the driving mechanism drives the in vitro magnetic field generating element to move upon the locating probe is being placed at the center of the pre-cut mucosa to be dissected; and the in vitro magnetic field generating element stops at its current position and does not move again upon the magnetic field intensity detected by the locating probe reaching a peak value;

step S2, upon the in vivo device being placed on the edge of the mucosa to be dissected, the clip clips the mucosa to be dissected and the in vitro magnetic field generating element generates an in vitro magnetic field, the control system builds a carrier coordinate system O-XYZ of an in vitro magnetic dipole, and defines the 2 rotational degrees of freedom of the in vitro magnetic dipole in the carrier coordinate system as rotation about the X-axis and Z-axis, respectively; where the direction of the in vitro magnetic dipole is taken as the Y-axis direction, and the X-axis and Z-axis are the coordinate axes selected in the plane perpendicular to the Y-axis, and the X-axis, Y-axis and Z-axis conform to the right-hand rule;

step S3, the driving mechanism drives the in vitro magnetic field generating element to make the in vitro magnetic dipole rotate a combination of the 2 rotational degrees of freedom, the magnetic auxiliary member moves and/or rotates accordingly with the rotation of the in vitro magnetic field generating element, while the magnetic auxiliary member is adjusted to a position P1' flat against the mucosa to be dissected, and the control system records the position of the in vitro magnetic dipole as a first flat position P1;

the driving mechanism drives the in vitro magnetic field generating element to make the in vitro magnetic dipole rotate a combination of the 2 rotational degrees of freedom, the magnetic auxiliary member moves and/or rotates accordingly with the rotation of the in vitro magnetic field generating element, while the magnetic auxiliary member is adjusted to another position P2' flat against the mucosa to be dissected, and the control system records the position of the in vitro magnetic dipole as a second flat position P2, the first flat position P1 and the second flat position P2 forming a plane S, the position P1' and the position P2' forming a plane S';

step S4, the control system updates the carrier coordinate system of the in vitro magnetic dipole according to the first flat position P1 and the second flat position P2: P2 as the Y axis, Z=P2×P1 as the Z axis of the coordinate system, the X-axis is determined by the right-hand rule; the control system defines the 2 rotational degrees of freedom of the in vitro magnetic dipole in the updated carrier coordinate system: the 1st' rotational degree of freedom is rotation about the Z-axis of the updated carrier coordinate system, and the 2nd' rotational degree of freedom is rotation about the rotation obtained by a cross product of the normal vector of the plane S and the second flat position P2;

step S5, the driving mechanism drives the in vitro magnetic dipole to rotate the 1st' rotational degree of freedom in the plane S, and accordingly, the magnetic auxiliary member rotates in the plane S' of mucosa, and the magnetic auxiliary member is adjusted to the center of the plane S' of mucosa or other initial position of curling; and step S6, the driving mechanism drives the in vitro magnetic dipole to rotate the 2nd' rotational degree of freedom, and accordingly the magnetic auxiliary member starts to curl mucosa.

* * * * *